US006476001B1

(12) United States Patent
Hellerqvist et al.

(10) Patent No.: US 6,476,001 B1
(45) Date of Patent: Nov. 5, 2002

(54) FACILITATION OF REPAIR OF NEURAL INJURY WITH CM101/GBS TOXIN

(75) Inventors: Carl G. Hellerqvist, Brentwood; Artur W. Wamil; Barbara D. Wamil, both of Nashville, all of TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/364,620

(22) Filed: Jul. 29, 1999

Related U.S. Application Data

(63) Continuation of application No. PCT/US98/01851, filed on Jan. 29, 1998, which is a continuation-in-part of application No. 08/791,857, filed on Jan. 29, 1997.

(51) Int. Cl.[7] .................... A01N 43/04; A61K 31/715; A61K 39/09; A61K 39/085

(52) U.S. Cl. .................... 514/54; 424/237.1; 424/244.1

(58) Field of Search .................... 424/198.1, 85.1, 424/237.1, 244.1; 514/54

(56) References Cited

U.S. PATENT DOCUMENTS

| | | | | |
|---|---|---|---|---|
| 4,242,326 A | | 12/1980 | Sugawara et al. | |
| 4,882,317 A | | 11/1989 | Marburg et al. | |
| 4,895,838 A | | 1/1990 | McCluer et al. | |
| 5,010,062 A | | 4/1991 | Hellerqvist et al. | |
| 5,225,331 A | | 7/1993 | Jennings et al. | |
| 5,302,386 A | | 4/1994 | Kasper et al. | |
| 5,382,514 A | | 1/1995 | Passaniti et al. | |
| 5,858,991 A | * | 1/1999 | Hellerqvist et al. | 514/54 |

FOREIGN PATENT DOCUMENTS

| | | |
|---|---|---|
| EP | 0 445 280 B1 | 9/1991 |
| WO | WO 94/10202 | 5/1994 |
| WO | WO 94/20085 | 9/1994 |
| WO | WO 96/25171 | 8/1996 |
| WO | WO 97/41844 | 11/1997 |
| WO | WO 98/14603 | 4/1998 |

OTHER PUBLICATIONS

Lundberg et al., Neurobiol. Dis., 3(1):33–50, Feb., 1996.*

Lundberg et al., Brain Res., 737(1–2):295–300, Oct., 1996.*

Campbell et al., Neuron, 15(6):1259–73, Dec., 1995.*

Xu et al., Exp. Neurol., 134(2):261–72, Aug., 1995.*

Logan et al., Br. Res., 587(2):216–25, 1992.*

Nadal et al., PNAS 92(5):1426–30, 1995.*

Augustin et al., "Ovarian Angiogenesis: Phenotypic Characterization of Endothelial Cells in a Physiological Model of Blood Vessel Growth and Regression," *Am. J. Pathol.,* 147(2):339–351, (1995).

Battegay, "Angiogenesis: Mechanistic Insights, Neovascular Diseases, and Therapeutic Prospects," *J. Mol. Med.,* 73:333–346, (1995).

Brown et al., "Overexpression of Vascular Permeability Factor (VPF/VEGF) and its Endothelial Cell Receptor in Delayed Hypersensitivity Skin Reactions," *J. Immunol.,* 154(6):2801–2807, (1995).

Brown et al., "Increased Expression of Vascular Permeability Factor (Vascular Endothelial Growth Factor) in Bullous Pemphigoid, Dermatitis Herpetiformis, and Erythema Multiforme," *J. Invest. Dermatol.,* 104(5):744–749, (1995).

Cheng et al., "Spinal Cord Repair in Adult Paraplegic Rats: Partial Restoration of Hind Limb Function," *Science,* 273:510–513 (1996).

Dvorak et al., "Vascular Permeability Factor/Vascular Endothelial Growth Factor: An Important Mediator of Angiogenesis in Malignancy and Inflammation," *Int. Arch. Allergy Immunol,* 107:233–235, (1995).

Dvorak et al., "Vascular Permeability Factor/Vascular Endothelial Growth Factor, Microvascular Hypermeability, and Angiogenesis," *Am. J. Pathol.,* 146(5):1029–1039, (1995).

Ferrara, "The Role of Vascular Endothelial Growth Factor in Pathological Angiogenesis," *Breast Cancer Res. Treat.,* 36:127–137, (1995).

Ferrara et al., "Vascular Endothelial Growth Factor, a Specific Regulator of Angiogenesis," *Curr. Opin. Nephrol. Hypertens,* 5(1):35–44, (1996).

Folkman, "Angiogenesis in Cancer, Vascular, Rheumatoid and Other Disease," *Nature Medicine,* 1(1):27–31, (1995).

Folkman, "Diagnostic and Therapeutic Applications of Angiogenesis Research," *C. R. Acad. Sci. Paris, Science de la vie,* 316:914–918, (1993).

Folkman et al., "Angiogenic Factors," *Science,* 235:442–447, (1987).

Hellerqvist et al., "Early Results of a Phase I Trial of CM101 in Cancer Patients," Proceedings of the American Assoc. of Cancer Research Annual Meeting, 36:224, (1995).

Hellerqvist et al., "Studies on Group B β–Hemolytic Streptococcus I. Isolation and Partial Characterization of an Extra–Cellular Toxin," *Pediatr. Res.,* 15:892–898, (1981).

Hellerqvist et al., "Cytokine Production in Cancer Patients Receiving the Anti–Neovascularization Drug CM–101," *Proceedings of ASCO,* Abstract #1592, vol. 14, (1995).

Hellerqvist et al., "Antitimor Effects of GBS Toxin: A Polysaccharide Exotoxin From Group B β–Hemolytic Streptococcus," *J. Canc. Res. Clin. Oncol.,* 120:63–70, (1993).

(List continued on next page.)

*Primary Examiner*—Gary L. Kunz
*Assistant Examiner*—Sharon Turner
(74) *Attorney, Agent, or Firm*—Cooley Godward LLP

(57) ABSTRACT

Neural injury may be advantageously treated with CM101, a polysaccharide toxin isolated from Group B β-hemolytic Streptococcus bacteria. CM1O1 treatment aids in the re-establishment of neuronal connectivity, at least partially inhibits scar formation, and increases the probability of survival during the critical period following injury to the central nervous system. Preexisting neural injuries having scar tissue are ameliorated by surgical excision of the scar tissue in conjunction with administration of CM101.

32 Claims, 7 Drawing Sheets

OTHER PUBLICATIONS

Hellerqvist et al., "CM101 Induces a Complement–Activated Inflammatory Responses Targeting Tumor Neovasculature," *Proceedings of the American Association for Cancer Research,* Abstract #3328, (1996).

Hellerqvist et al., "Molecular Basis for Group B β–Hemolytic Streptococcal Disease," *Proc. Natl. Acad. Sci. USA,* 84:51–55, (1987).

Hellerqvist et al., "Preliminary Results of a Phase I Trial of CM101 in Cancer Patients," *J. of Cellular Biochemistry,* Supp 19B, p. 26, (1995).

Herblin et al., "Inhibition of Angiogenesis as a Strategy for Tumor Growth Control," *Molecular and Chemical Neuropathology,* 21:329–336, (1994).

Houle et al., "Axonal Regeneration by Chronically Injured Supraspinal Neurons Can Be Enhanced by Exposure to Insulin–Like Growth Factor, Basic Fibroblast Growth Factor Beta," *Restorative Neurol. And Neurosci.,* 10:201–215, (1996).

Jennings et al., "Structural Determination and Serology of the Native Polysaccharide Antigen of Type–III Group β–Streptococcus," *Can. J. Biochem.,* 58(2):112–120, (1980).

Kim et al., "Inhibition of Vascular Endothelial Growth Factor–Induced Angiogenesis Suppresses Tumor Growth in Vivo," *Nature,* 362:841–844, (1993).

Klagsbrun et al., "Regulators of Angiogenesis," *Annu. Rev. Physiol.,* 53:217–239, (1991).

Mollgard et al., "Development of Spinal Cord in the Isolated CNS of a Neonatal Mammal (the Opossum *Monodelphis Domestica*) Maintained in Lonterm Culture," *J. Neurocyt.,* 23:151–165, (1994).

Moses et al., "Identification of an Inhibitor of Neovascularization from Cartilage," *Science,* 248:1408–1410, (1990).

Nicholls et al., "Reflexes, Fictive Respiration and Cell Division in the Brain and Spinal Cord of the Newborn Opossum, *Monodelphis Domestica,* Isolated and Maintained in Vitro," *J. Exp. Biol.,* 152:1–15, (1990).

Nicholls et al., "Regeneration of Immature Mammalian Spinal Cord After Injury," *Trends Neurosci.,* 19(6):229–234, (1996).

Ondrick et al., "Angiogenesis," *Clinics in Podiatric Medicine and Surgery,* 9(1):185–203, (1992).

Ono et al., "Induction of Human Microvascular Endothelial Tubular Morphogenesis by Human Keratinocytes: Involvement of Transforming Growth Factor Alpha," *Biochem. Biophys. Res. Commun.,* 189(2):601–609, (1992).

Parkinson, "Present Status of Biological Response Modifiers in Cancer," *Amer. J. Med.,* 99 (Suppl. 6A):54S–56S, (1995).

Plate et al., "Molecular Mechanisms of Developmental and Tumor Angiogenesis," *Brain Pathol.,* 4:207–218, (1994).

Polverini, "The Pathophysiology of Angiogenesis," *Crit. Rev. Oral Biol. Med.,* 6(3):230–247, (1995).

Sato et al., "Actions of TNF and IFN–γ on Angiogenesis in Vitro," *J. Invest. Derm.,* 95(6 Supp.):85S–89S, (1990).

Seil, "Neural Regeneration: 6$^{th}$ International Symposium," *The Neuroscientist,* 2(3):143–44, (1996).

Senger et al., "Vascular Permeability Factor (VPF, VEGF) in Tumor Biology," *Cancer and Metastasis Reviews,* 12:303–324, (1993).

Senger et al., "Vascular Permeability Factor, Tumor Angiogenesis and Stroma Generation," *Invasion Metastasis,* 14:385–394, (1994–1995).

Stewart et al., "The Intact Central Nervous System of the Newborn Opossum in Long–Term Culture: Fine Structure and GABA–Mediated Inhibition of Electrical Activity," *J. Exp. Biol.,* 161:25–41, (1991).

Sotelo et al., "The Reconstruction of Cerebellar Circuits," *Trends Neurosci.,* 14(8):350–355, (1991).

Turco, "Intravenous Admixtures," *Remington's Pharmaceutical Sciences,* 18$^{th}$ ed., chapter 85:1570–1580, Mach Publ., (1990).

Van den Pol et al., "Excitatory Actions of GABA After Neuronal Trauma," *J. Neurosci.,* 16(13):4283–4292, (1996).

Wamil et al., "Leukocyte Activation in Response to CM101 Treatment of Cancer Patients," *Proceedings of the American Association for Cancer Research,* Abstract #3329, (1996).

Wamil et al., "Phenytoin Blocks N–Methyl–D–Aspartate Responses of Mouse Central Neurons," *J. Pharmacol. Exp. Ther.,* 267(1):218–227, (1993).

Wamil et al., "Uses–, Concentration–, and Voltage–Dependent Limitations by MK–801 of Action Potential Firing Frequency in Mouse Central Neurons in Cell Culture," *J. Pharmacol. Exp. Ther.,* 260:376–383, (1992).

Wamil et al., "Effect of Temperature on Limitation by MK–801 of Firing of Action Potentials by Spinal Cord Neurons in Cell Culture," *European J. of Pharmacol.,* 230:263–269, (1993).

Ye et al., "Treatment of Chronically Injured Spinal Cord with Neurotrophic Factors Can Promote Axonal Regeneration From Supraspinal Neurons," *Experimental Neurology,* 143:70–81, (1997).

Young, "Spinal Cord Regeneration," *Science,* 273:451, (1996).

Zhoa et al., "Neurotization of Motor Nerves Innervating the Lower Extremity by Utilizing the Lower Intercostal Nerves," *J. of Reconstructive Microsurgery,* 13(1):39–45, (1997).

* cited by examiner

FACILITATION OF REPAIR OF NEURAL INJURY WITH CM101/GBS TOXIN

CROSS-REFERENCE TO RELATED APPLICATIONS

This application is a continuation of PCT/US98/01851, filed Jan. 29, 1998, which is a continuation-in-part of U.S. Ser. No. 08/791,857, filed Jan. 29, 1997.

INTRODUCTION

1. Technical Field

This invention relates to therapy for enhancing repair of neural injury in the central nervous system or the peripheral nervous system.

2. Background

Neural injury caused by physical trauma, ischemia, or disease can result in profound disability or death. Such disabilities, which may be physical and/or mental, include loss of movement, impaired sensory perception, loss of cognitive functions, seizures, and emotional and personality disorders. Given the incidence of death and the prevalence and possible severity of survivors' disabilities, neural injury takes a heavy toll on individuals and society. Accordingly, there is a need for treatments which facilitate the repair of damaged nerves and neuronal pathways. At present, there is no effective treatment for central nervous system (CNS) injuries.

Brain physical trauma, spinal cord compression or transection, ischemia, or surgery cause hypoxia which initiates a cascade of molecular events leading to neural injury (Liu, X. Z. et al., Neuronal and glial apoptosis after traumatic spinal cord injury, *J. Neurosci.,* 17:5395–5406 (1997); Olsson, Y. et al., Release of endogenous neurochemicals may increase vascular permeability, induce edema and influence cell changes in trauma to the spinal cord, *Progress in Brain Res.,* 91:197–203 (1992); Crowe, M. J. et al., Apoptosis and delayed degeneration after spinal cord injury in rats and monkeys, *Nature Med.,* 3:73–76 (1997)). Despite receiving medical attention, many patients die in the first few days following a serious CNS injury. For those patients that survive their injuries, prognosis depends on the ability of the remaining neurons to adapt new functions because, with current technology, neuronal connectivity is rarely restored. Because neural adaptation is slow and frequently incomplete, the potential benefit of a treatment which facilitates neural repair and the re-establishment of neuronal connectivity would be tremendous as would the benefit provided by a treatment that reduces the probability that a patient will die during the critical post-injury period.

Neurons in the peripheral nervous system can regenerate and re-innervate their targets. However, scar tissue that forms as a result of the injury can obstruct the growth of regenerating peripheral nerves and interfere with recovery of neural function. Because repair of neural injury can be facilitated by inhibiting scar formation, there is a need for a treatment to minimize scar formation in the peripheral nervous system.

Regeneration of nerves in the mammalian CNS is more limited. In the adult mammalian CNS, neural regeneration was thought nearly impossible until recently (Snell, L. and Schwab, M. E., Sprouting and regeneration of lesioned cortical spinal tract fibers in the adult rat spinal cord, *Eur. J. Neurosci.,* 5:1156–1161 (1993); Cheng, H. et al., Spinal cord repair in adult paraplegic rats: partial restoration of hind limb function, *Science,* 273:510–513 (1996); Young, W., Spinal cord regeneration, *Science,* 273:451 (1996); Olson, L., Regeneration in the adult central nervous system: Experimental repair strategies, *Nature Med.,* 3(12):1329–1335 (1997); Li, Y., et al., Repair of adult rat cortical spinal tract by transplant of olfactory and ensheathing cells, *Science,* 277:2000–2002 (1997)). Since adult mammalian CNS neurons have been shown to be capable of growing and developing synaptic connections when placed in a different setting, it has been hypothesized that the CNS contains inhibitors of neuronal regeneration. Neuronal growth in the CNS may also be retarded by gliosis, a process in which glial scars are formed in the healing CNS as a result of the proliferation of astrocytes and microglia and the infiltration of macrophages. Posttraumatic epilepsy, which can arise up to several years after head trauma, is also associated with glial cerebromeningeal scars (McNamara, J. O., Cellular and molecular basis of epilepsy, *J. Neurosci.,* 14:3413–3416 (1994)). Since minimizing gliosis can both facilitate neuronal regeneration and decrease the likelihood of posttraumatic epilepsy, there is a need for treatments which inhibit gliosis.

The failure of persons with CNS injuries, particularly spinal cord injuries, to regain neural function is at least partially due to steric interference by gliosis and subsequent scar formation. There is a need for a treatment to facilitate repair of CNS injuries by minimizing gliosis and scarring. The need is particularly great for a treatment that, in addition to facilitating healing of recent neural injuries, could aid in the restoration of neural function in a person with a preexisting neural injury.

SUMMARY OF THE INVENTION

The present invention is a method of treating neural injury by administering a GBS toxin, a nontoxic polysaccharide derived from group B β-hemolytic Streptococcus bacteria.

One aspect of the present invention is the administration of a GBS toxin to a patient with a neural injury to promote the re-establishment of neuronal connectivity. The present invention demonstrates that GBS toxin administration facilitates enhanced transfer of electrical impulses across a site of neural damage. GBS toxin-mediated enhancement of neuronal connectivity is functionally significant: animals treated with GBS toxin regained the ability to walk within a few days of neuronal injury whereas untreated animals with identical injuries remained paralyzed.

Another aspect of the present invention is the administration of a GBS toxin to minimize scar formation in patients with neuronal injury. Minimizing scar formation allows more complete recovery of neuronal connectivity. In addition, by reducing gliosis, GBS toxin administration to patients with head trauma reduces the likelihood of post-traumatic epilepsy and other complications.

A third aspect of the invention is the administration of a GBS toxin to increase the probability of a patient's survival following CNS injury.

A fourth aspect of the invention is the administration of a GBS toxin to minimize formation of new scars following surgical excision of existing scar tissue associated with a preexisting neural injury.

An article of manufacture including GBS toxin, and particularly CM101, along with instructions for treatment, and a method of making the article are also disclosed.

According to the present invention, GBS toxin may be used to improve the quality of the healing process in both the CNS and the peripheral nervous system.

BRIEF DESCRIPTION OF THE DRAWINGS

FIG. 1A diagrams the two microelectrode system used in the experiments: the microelectrode to the left of the crush site fired a single electric pulse (arrow) and the microelectrode on the right recorded the changes in membrane potential induced by the pulse. The experiments were carried out one day (B&C) and five days (D&E) after injury on untreated, traumatized CNSs (B&D) and traumatized CNSs that were treated with 0.3 μg/ml CM101 (C&E). Calibrations at right apply throughout.

DESCRIPTION OF SPECIFIC EMBODIMENTS

Figure 1A:
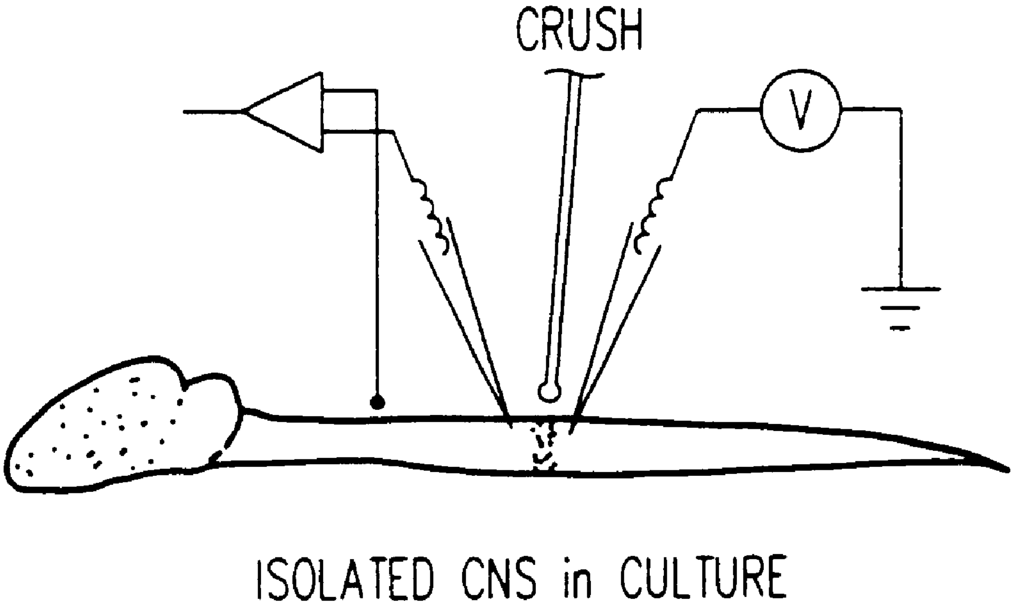
FIGS. 1A–1E show the results of electrophysiological experiments on isolated CNSs with spinal cord crush injuries.

CM101, a GBS toxin, is a polysaccharide molecule isolated from group B β-hemolytic Streptococcus (GBS). Specifically, pathogenic group B β-hemolytic Streptococcus produces a polysaccharide exotoxin. This exotoxin is the putative agent for early onset disease in neonatal humans. It is believed that receptors for CM101 are present primarily on the lungs of newborns, making them susceptible to early onset disease, but that the receptors are lost approximately four to seven days after birth.

Isolated and purified CM101 has been shown to have toxic effects on sheep experimental models that mimic GBS infant pneumonia (Hellerqvist, C. G. et al., Studies on group B β-hemolytic streptococcus I. Isolation and partial characterization of an extra-cellular toxin., *Pediatr. Res.,* 12:892–898 (1981)). In the sheep model for neonatal early onset disease, GBS toxin causes pulmonary hypertension, increased pulmonary vascular permeability, granulocytopenia, and pulmonary sequestration of granulocytes.

CM101 has a molecular weight of approximately 300,000 Daltons and comprises N-acetyl-galactosamine, N-acetyl-glucosamine, glucose, galactose, and mannose residues. Carboxylic acid residues are also believed to be an integral part of the molecule. Repeating active epitopes most likely play an important role in the pathophysiological response to CM101 by crosslinking receptors on target endothelium (Hellerqvist, C. G. et al., Early Results of a Phase I Trial of CM101 in Cancer Patients., *Proceedings of the American Association of Cancer Research Annual Meeting* (1995)).

A method of purification of a GBS toxin is provided in U.S. Pat. No. 5,010,062. Preferably, however, the CM101 is purified according to the method taught in International Application No. PCT/US97/17535, incorporated herein by reference.

A source for GBS starting material for use in the method of the present invention may be obtained by culturing strains of Group B β-hemolytic Streptococcus bacteria that have recently infected or are capable of infecting newborn infants. Isolates of such strains may be obtained from the blood or cerebrospinal fluid of infected infants.

Without limitation to a particular theory, it is believed that GBS toxin, and specifically CM101, plays an important role in the treatment of neural injury because it facilitates the regeneration of neuronal connectivity by inhibiting glial cell proliferation. Trauma to the CNS is known to cause hypoxia (Liu et al., 1997), and this causes the release of vascular endothelial growth factor (VEGF). VEGF stimulates endothelial cells to dedifferentiate and begin to form new vasculature. The newly formed vasculature facilitates glial cell proliferation which gives rise to scars that physically interfere with the reformation of neuronal contacts. CM101 treatment impairs the proliferation of glial cells, thereby lessening gliosis (the formation of scars in the healing CNS). CM101-mediated impairment of glial cell proliferation is indirect and occurs by binding of CM101 to dedifferentiated angiogenic endothelial cells, thus targeting them for complement-mediated destruction, and by down-regulation of VEGF transcription (Wamil, B. D. et al., CM101 inhibits VEGF induced tumor neovascularization as determined by MRI and RT-PCR, *AACR Proceedings,* 38:237 (1997)). Since glial scars sterically interfere with neuronal reconnection of damaged axons, treatment with CM101 fosters the reestablishment of neuronal connectivity and permits recovery of vital organ function as well as motor and sensory function.

The present invention is useful for treating central nervous system injuries and peripheral nervous system injuries. It facilitates post-injury re-establishment of neuronal connectivity by inhibiting scar formation and by enhancing neuronal regeneration. In addition to treatment of trauma, surgery, and ischemia patients in the minutes or hours preceding or following the infliction of the injury, CM101 finds use in patients with pre-existing neural injury, an injury that has been in existence for more than two weeks. These patients receive CM101 to inhibit the formation of new scars after microsurgical excision of existing scar tissue. These patients may receive infusions of nerve growth factors such as IGF-1, bFGF or TGFβS (Houle, J. et al., Axonal regeneration by chronically injured supraspinal neurons can be enhanced by exposure to insulin-like growth factor, basic fibroblast growth factor or transforming growth factor beta, *Restorative Neurol. Neurosci.,* 10(4):205–215 (1996)), or BDNF, NT-3 (Grill, R. et al., Cellular delivery of neurotrophin-3 promotes corticospinal axonal growth and partial functional recovery after spinal cord injury, *J. Neurosci.,* 17:5560–5572 (1997)), CNTF (Ye, J-H. and Houle, J., Treatment of the chronically injured spinal cord with neurotrophic factors can promote axonal regeneration from supraspinal neurons, *Exp. Neurol.,* 143(1):70–81 (1997); Grill et al., 1997) or transplants of neural progenitor cells (Lundberg, C. et al., Conditionally immortalized neural progenitor cell lines integrate and differentiate after grafting to the adult rat striatum: A combined autoradiographic and electron microscopic study, *Brain Res.,* 737(1-2):295–300 (1996)) to increase neuronal regeneration at the excision site. For patients with head trauma, CM101 treatment decreases the likelihood of posttraumatic epilepsy associated with cerebromeningeal scarring.

Since CM101 promotes neuronal repair and facilitates the re-establishment of neuronal connectivity, it provides a method for treating persons with diseases characterized by neuronal degeneration or impairment of neuronal connectivity. These diseases include Alzheimer's disease, Pick's disease, Parkinson's disease, striatonigral degeneration, Shy-Drager syndrome, Hallervorden-Spatz syndrome, progressive supranuclear palsy, olivopontocerebellar atrophy, Friedreich's ataxia, ataxia-telangiectasia, amyotrophic lateral sclerosis, primary lateral sclerosis, progressive muscular atrophy, progressive bulbar palsy, pseudobulbar palsy, Werdnig-Hoffman disease, Kugelberg-Welander syndrome, multiple sclerosis, and perivenous encephalomyelitides. The benefit of CM101-mediated enhanced neuronal repair to patients suffering from diseases such as these is appreciable.

One of the methods used to determine CM101's effect on neuronal repair is an in vitro assay of GABA-mediated alteration of neuron membrane potential. This assay is based on the observation that, although healthy neurons hyperpolarize when exposed to GABA, neurons that have an unrepaired injury depolarize when GABA is applied. Since the amplitude of the depolarization reflects the severity of the neuronal damage, response to GABA over time provides a measure of the kinetics of neuronal sprouting and repair. This assay demonstrates that CM101 enhances neuronal regeneration. The GABA assay has utility for the testing of other compounds for their abilities to positively or negatively affect repair of neuronal injury.

GBS toxin as used herein is defined as any fraction or component isolated from natural or lysed GBS bacteria, or derived from media supernatants of lysed and/or autoclaved GBS bacteria, and which has a biological activity as evidenced by induction of respiratory distress in the sheep assay (Hellerqvist, C. G. et al., Studies on group B β-hemolytic streptococcus I. Isolation and partial characterization of an extra-cellular toxin., *Pediatr. Res.,* 12:892–898 (1981)) or activation of, complement and binding to neovasculature as demonstrated by a peroxidase-antiperoxidase (PAP) assay of a tumor tissue specimen (Hellerqvist, C. G. et al., Anti-tumor effects of GBS toxin: a polysaccharide exotoxin from group B β-hemolytic streptococcus, *J. Canc Res. Clin. Oncol.,* 120:63–70 (1993); and Hellerqvist, C. G. et al., Early Results of a Phase I Trial of CM101 in Cancer Patients., *Proceedings of the American Association of Cancer Research Annual Meeting* (1995)). GBS toxin also means any synthetic polysaccharide with the same structure or function as any GBS-derived molecule with the aforementioned activity.

Substantially pure GBS toxin means a preparation in which GBS toxin is greater than 40% pure (e.g., present in a concentration of at least about 40% by weight), preferably at least approximately 60% pure, more preferably at least approximately 90% pure, and most preferably at least approximately 95% pure. Dosages of lower purity GBS toxin should be altered accordingly. The purity of GBS toxin is discussed in greater detail in International Application No. PCT/US97/17535.

The CM101 or other GBS toxin is preferably combined with a pharmaceutically acceptable carrier and administered to a patient systemically. The carrier is preferably one that is readily mixed with CM101 to form a composition that is administrable by intravenous (IV) means. Thus, the carrier is preferably saline, which may have other pharmaceutically acceptable excipients included to ensure its suitability for intravenous administration. The resulting composition will be sterile and will have acceptable osmotic properties. In general, a suitable IV formulation is prepared in accordance with standard techniques known to one of skill in the art. For example, Chapter 85 entitled "Intravenous Admixtures" by Salvatore J. Turco in the Eighteenth Edition of *Remington's Pharmaceutical Sciences,* Mach Publishing Co. (1990), incorporated herein by reference, provides standard techniques for preparing a pharmaceutically acceptable IV composition useful in accordance with this invention. Other dosage forms to administer CM101 may also be used. As an alternative to systemic administration, CM101 may be administered locally to a site. Administration of CM101 to the patient may occur before, during, and/or after infliction of the neural injury. Preferably, CM101 is administered within an appropriate temporal window following the injury. Administration of CM101 soon after the injury occurs is most preferred. For example, administration within 1 day, or preferably within six hours is best. Administration of CM101 soon after CNS injury is necessary to increase the probability (relative to patients with similar injuries who do not receive CM101 ) that the patient will survive the first few days following the injury. While the length of this "critical post-injury period" varies according to the type and magnitude of the injury, survival at 72, 98 and 120 hours following injury are significant milestones.

The amount of CM101 that is administered to a patient is an amount that is sufficient to aid in the reestablishment of neuronal connectivity and to minimize scarring. A preferred dosage range is 1 to 100 μg/kg body weight. A more preferred dosage range, however, is 1 μg/kg to 50 μg/kg body weight, and most preferred is a dosage in the range of 1 μg/kg to 25 μg/kg. It will be understood, however, that the specific dose level for any particular patient will depend on a variety of factors including the age, body weight, general health, sex, diet, and severity of the neural injury. Each dosage is preferably administered in an infusion of up to 120 minutes, with 5 to 60 minutes being the preferred duration range, and 5 to 30 minutes being the most preferred dosage range. Once weekly treatment is preferred, and is likely to be all that is necessary for evidence of results.

Neural injury exists when a portion of a neuron or nerve, a bundle of fibers or processes, is punctured, torn, severed, crushed, bruised, or otherwise incapacitated in its abilities to transmit or receive electrochemical signals. Re-establishment establishment of neuronal connectivity involves the reformation of normal synaptic structure or the resumption of normal synaptic function. This can be assessed by neurological examination, neurologic diagnostic procedures such as electroencephalography, magnetic resonance imaging and CT scan, or electrophysiological recordings, or synaptic visualization.

Another aspect of the present invention is an article of manufacture, such as a kit, and a method for making the article of manufacture. The article includes a pharmaceutical composition comprising a GBS toxin, and particularly CM101, and a pharmaceutically acceptable carrier. The pharmaceutical composition may be placed in a suitable container, as is well known in the art. Also included are instructions for treatment of patients according to the methods of the present invention.

The invention now being generally described may be better understood by reference to the following examples, which are presented for illustration only and are not to be construed as limitations on the scope or spirit of the present invention.

EXAMPLES

Example 1

CM101 Enhances the Reestablishment of Neuronal Connectivity in Traumatized, Isolated Central Nervous Systems The effects of CM101 on the reestablishment of neuronal connectivity and the reacquisition of neural function were investigated in isolated and traumatized central nervous systems.

Isolated CNS cultures were prepared according to modified published methods (Nicholls et al., 1990: Stewart et al., 1991). The brain and spinal cord with attached dorsal and ventral roots were dissected out from embryonic mice E5 (gestation day 5), and a lesion was induced in the spinal cord by a gentle smash with surgical tweezers. The traumatized CNS preparations were cultured at room temperature (23–25° C.) for 5–7 days (Stewart et al., 1991; Mollgard et al., 1994). The culture medium was Eagle's Minimal Essential Medium (MEM) containing 0.2% fetal calf serum (GIBCO), 30 ng/rl NGF 7S (Sigma), 10 $\mu$/ml insulin, and 0.1 mg/ml gentamicin sulfate. After equilibration with incubator atmosphere containing 5% $CO_2$, the pH of the culture medium was 7.4. Medium was changed three times a week. In one group of isolated, traumatized CNSs (n=6), 0.3 $\mu$g/ml CM101 was added to the culture medium. The untreated group of isolated, traumatized CNSs (n=6) did not receive CM101. A control group of isolated CNSs (n=4) were spared the crush injury but were otherwise cultured identically to the untreated group.

After one day and five days in culture, electrophysiological experiments were performed to test synaptic connectivity at the crush site in the spinal cord. For those isolated traumatized CNSs that received CM101 during culturing, 0.3 $\mu$g/ml CM101 was present in the superfusate during the electrophysiological experiments. The experiments, which were conducted at 37° C., used a dual intracellular microelectrode recording technique (Wamil et al., 1994; Sotelo and Alvarado-Mallart, 1991). On each side of the spinal cord lesion, a microelectrode was impaled into the tissue (FIG. 1A). An experiment consisted of one microelectrode firing a single electric pulse (FIGS. 1B–E; arrowhead) and the other microelectrode recording any resulting depolarization or firing of action potentials on the other side of the injury.

On days 1, 2, 3, 4, 5, 10 and 16, isolated CNS tissue was harvested for histological examination of reconnected axons in adjacent segments of spinal cord.

Results

Figure 1B:
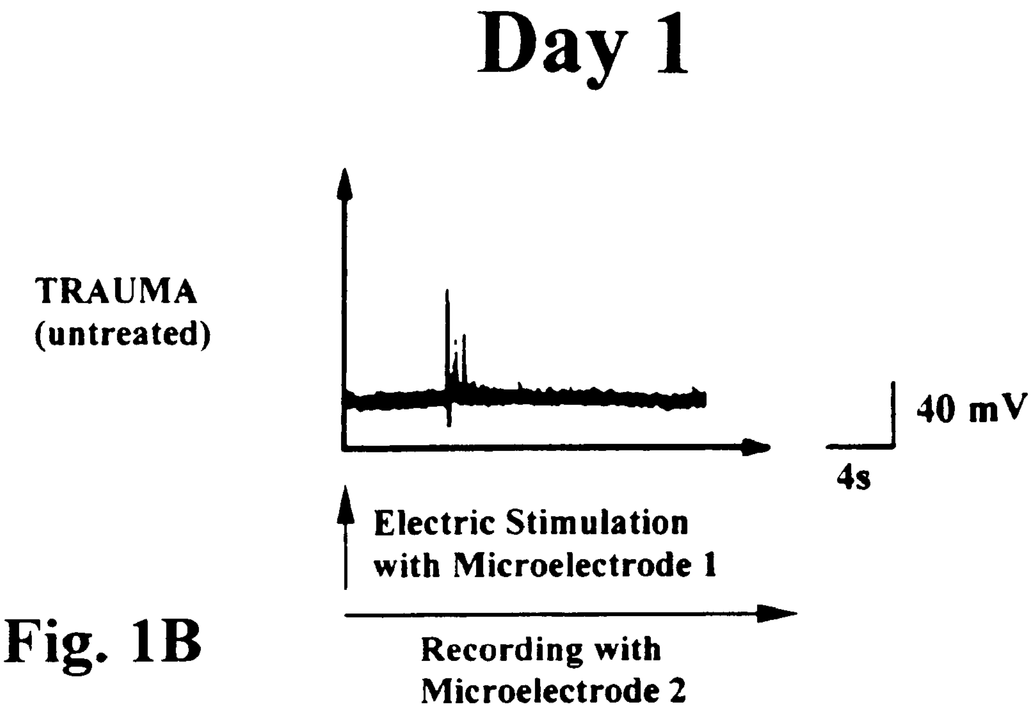
Figure 1C:
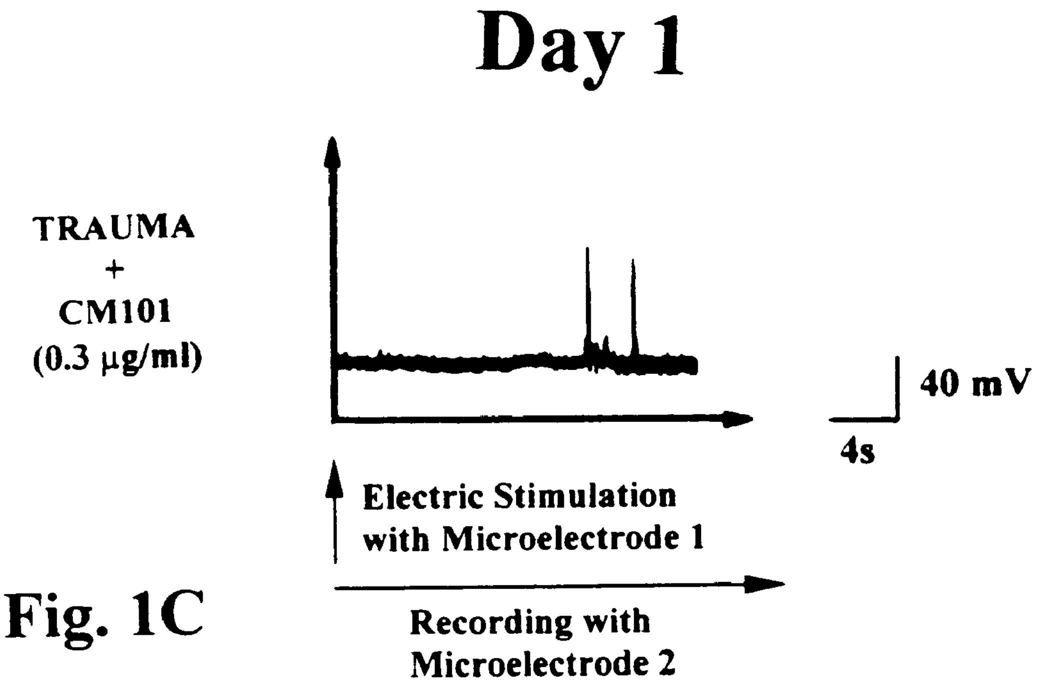

In untreated traumatized isolated CNSs after 1 day in culture, pulse stimulation (500 ms, 2–8 nA) produced a brief depolarizing response and few, if any, action potentials (FIG. 1B). The latency of this response was 4–20 s. By comparison, control CNS cultures had a 0.5–3 ms latency period (not shown). When the traumatized isolated CNSs treated with CM101 were stimulated with a pulse of 500 ms and 2–8 nA, a brief depolarizing response and rare or no action potentials resulted (FIG. 1C). The latency of this response was 10–20 s. These results show that both the untreated and CM101-treated CNSs have reestablished some neuronal connections across the crush site. No significant difference between the treated and untreated CNSs was observed after one day of CM101 treatment.

Figure 1D:
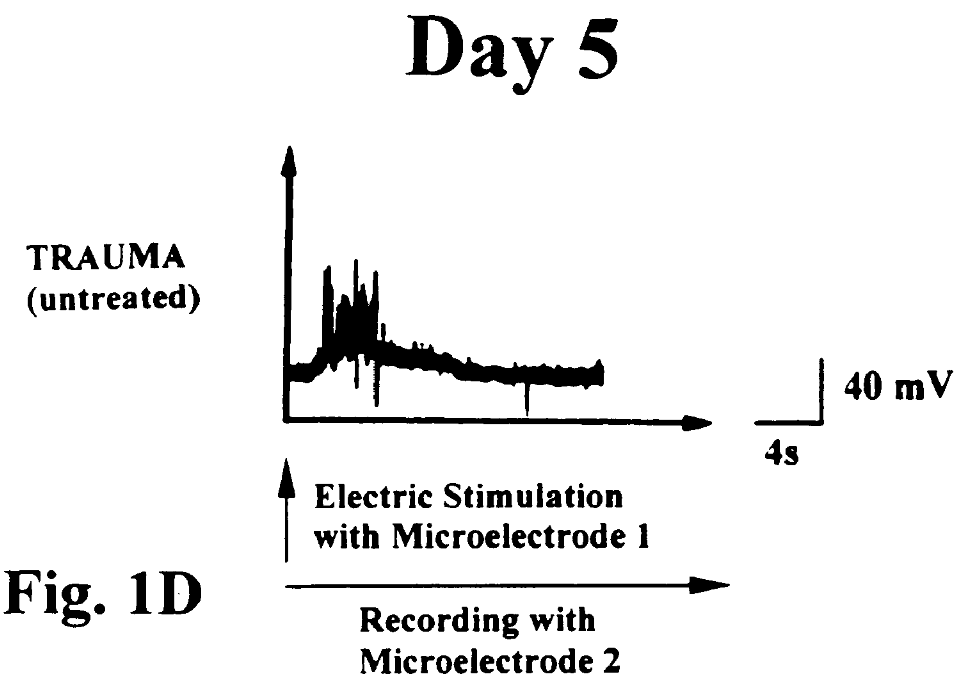
Figure 1E:
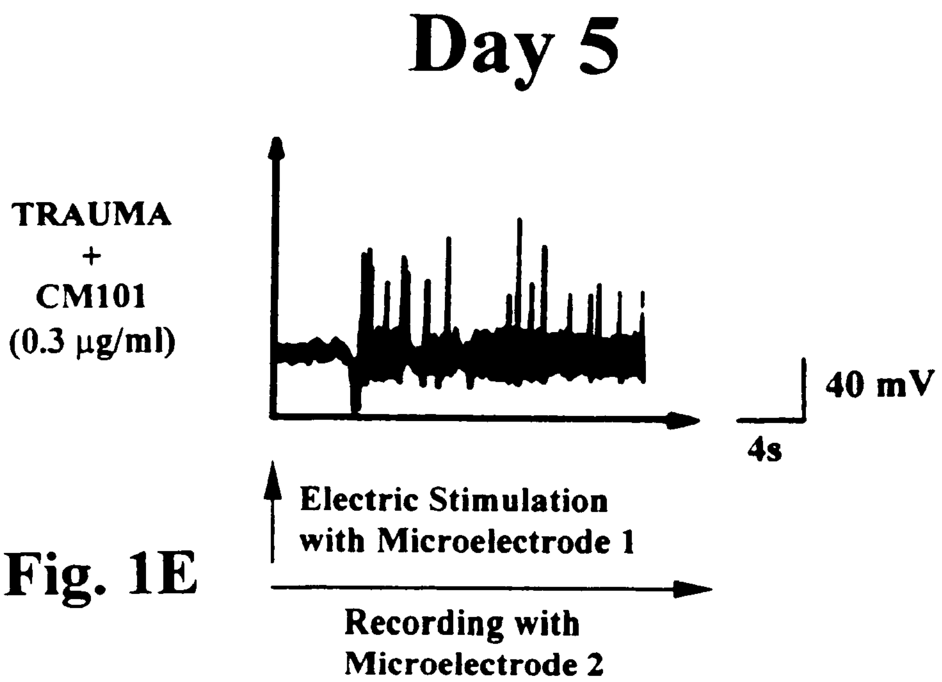

Five days after injury, similar stimulation of untreated, traumatized isolated CNSs produced larger amplitudes of depolarization, greater durations of response, and more intense firing of action potentials without postsynaptic potentials than were previously seen (compare FIG. 1D with FIG. 1B). The latency of firing was 2–4 s. Excitatory postsynaptic potentials (EPSPs) predominated over inhibitory postsynaptic potentials (IPSPs). In the CNSs that had been exposed to CM101 for the five days following injury, pulse stimulation produced intensive bidirectional activity (depolarization and hyperpolarization) in the form of excitatory APs and inhibitory hyperpolarization (FIG. 1E). This increase in excitatory and inhibitory activity relative to untreated traumatized CNSs shows that CM101 treatment facilitates neuronal reconnection and recovery of function of the spinal cord tracts.

Example 2

CM101 Facilitates the Recovery of Neural Function in Mice with Spinal Cord Compression Injuries The effects of CM101 on recovery from acute physical injury to the mammalian central nervous system were studied. A mouse model of spinal cord compression/crush injury was developed for the long-term observation of behavioral change resulting from acute trauma and treatment with CM101.

Four week old CD-1 mice were randomly designated to a control (n=6) or a CM101-treated (n=6) group. All mice received a skin incision and bilateral lesion of the spinal cord at the level of T11–T12. Within 5 minutes of trauma, all animals received an 100 $\mu$l injection into the dorsal tail vein. The CM101-treated animals received injections of 20, 60, or 120 $\mu$g/kg (n=2 per concentration), and the control animals received Dulbecco's phosphate-buffered saline. The animals were observed for seven days. When the mice died or were sacrificed after the seventh day, fragments of spinal cords with crush injury were saved for histopathological examination to determine standard time of gliosis, and the quality of neuronal connectivity.

Results

Within the first 48 hours, all animals were sedated and presented almost no locomotor activity. During the first four days after injury, all mice dragged their hind limbs, and no differences between control and CM101-treated mice were observed. Of the five mice which survived until day five, all three treated mice (two which received 20 $\mu$g/kg and one which received 60 $\mu$g/kg) were able to walk with moderate limping of both hind legs whereas the hind limbs of the control mice were paralyzed. One treated mouse (60 $\mu$g/kg CM101 ) and one control mouse survived seven days post trauma. The control mouse had paraplegia of the hind limbs on the seventh day. By comparison, the CM101-treated mouse was able to walk, to support body weight during forward stepping, and to climb a 60° inclined plane on day seven. The most noticeable defect in the CM101-treated mouse at day seven was a slight dragging of the toe on the left foot. These results indicate that CM101 facilitates the recovery of the function of the spinal cord after a compression or crush injury of the lower thoracic spine.

Example 3

CM101 Enables Adult Mice Paralyzed by Spinal Cord Compression Injuries to Regain Walking Ability and Increases Their Post-Injury Survival Rates The effects of CM101 treatment on recovery from spinal cord compression injury were verified and extended in a set of experiments similar to those reported in Example 2.

Each of 40 adult mice anesthetized with Ketamine and Xylazine (80:20, 50–100 mg/kg by intraperitoneal injection) received a 5–10 mm incision in the shaven, decontaminated skin above the vertebral column and the dorsal muscles were retracted, thus exposing the spinous processes of vertebrae T8–T13. The posterior processes of T10 and T11 were separated by microscissors and the intact dura mater was exposed. The spinal cord segment between T10 and T11 was gradually compressed with fine forcep tips (1 mm in width). Compression and the resulting crush damage was limited to one side of the spinal cord ("monoplegic") in 15 of the mice. The remaining 25 mice received bilateral compression injuries ("paraplegic") involving the entire spinal segment between T10 and T11. For all mice, compression reduced segment diameter from 2 mm to 0.1–0.2 mm. The procedure was completed by closing internal layers with surgical stitches and sealing the skin with sterile tissue glue. Each operated animal was allowed to recover from surgery with unlimited access to food and water. Care was taken during the post-operative period to minimize damage to the vertebral joints and soft tissues.

The surgically injured mice were randomly assigned to control and treatment groups. Control animals (monoplegic, n=5; paraplegic, n=9) received Dulbecco's phosphate-buffered saline ("PBS") whereas treated animals received either 30 μg/kg CM101 (monoplegic, n=4; paraplegic, n=8) or 60 μg/kg CM101 (monoplegic, n=5; paraplegic, n=8) diluted in PBS. All mice received 100 μl injections into the dorsal tail vein one hour after surgery and 2, 4, 6, 8 and 10 days after surgery.

Survival, functional deficits, and recovery from paralysis were assessed daily for the first 21 days following surgery and then weekly for up to 110 days. A modified form of the open-field walking scoring system developed by Cheng et al. (Spinal cord repair in adult paraplegic rats: partial restoration of hind limb function, *Science*, 273:510–513 (1996)) was used to measure each mouse's gross locomotor ability during a 3–5 minute testing period. One animal at a time was allowed to move freely inside a plastic tray (8"×11"×3"). Locomotor activity was videotaped, and animals were scored by two independent, blinded observers using a modified Tarlov scale (Cheng et al., 1996). This scale ranges from 0 (flaccid or spastic paralysis) to 5 (normal walking) and accurately reflects the standard pattern of recovery of locomotor function:

0—spastic and flaccid paralysis;
1—no spontaneous movement but recovery of sensory response to stimulus;
2—spontaneous, uncoordinated movement of groups of muscles;
3—movement of 2 or 3 of the 3 major joints in the hind limbs, and active support and either uncoordinated gait or short bouts of coordinated gait (limp walking);
4—coordinated walkling with small deficits in hind limbs and gait (includes walking on knuckles or the medial surface of the foot, moderate toe dragging, or walking on wide base); and
5—full recovery of normal walking function.

On day 6, two mice from each paraplegic group were sacrificed for histological analysis. Sagittal sections of spinal cord were stained with hematoxylin and eosine, and the degree of hemorrhage, fibrosis and gliosis in each animal was assessed and documented by photomicrography.

Twenty-one days after injury, magnetic resonance imaging ("MRI") was performed on the spinal cord of living control and treated mice to document the area of spinal damage and the process of healing. The spinal cord was visualized in 300 μm slices using a mouse size coil 1 inch in diameter at a 200 MHZ, 4.6 Tesla magnetic field.

Results

A. Survival

The numbers of surviving animals from day 0 (the day of surgery) through day 110 are shown in Table I. Each column in Table I represents the indicated day following surgery and each row represents the indicated experimental group (M:monoplegic; P:paraplegic). By day 1, 8 out of 14 control animals had died and all 26 treated mice were still alive. Within the next four days, 2 more control mice died and 2 of 26 treated animals died. Survival at day 6 averaged 92.3% in the treatment groups versus 28.6% in the control groups. Later that day, two mice from each paraplegic group were sacrificed for histology (indicated on Table I with asterisks). On day 28, 1 additional control animal died. The 20 remaining treated mice and sole surviving control mouse were still alive by day 35. By day 110, there were no survivors of the original 14 control mice (two of which were sacrificed on day 6) but 17 of the 26 treated mice (four of which were sacrificed on day 6) were still alive. Thus, the data provide strong evidence that intravenous administration of CM101 provides significant protection from early fatality associated with traumatic spinal cord injury. In particular, the probability that a treated mouse will survive five or more days after injury is much higher that the survival probability for a control mouse.

TABLE I

Animal Survival Following Spinal Cord Injury

| Experimental Group | Day | | | | | | | | | | | | | | | |
|---|---|---|---|---|---|---|---|---|---|---|---|---|---|---|---|---|
| | 0 | 1 | 2 | 3 | 5 | 6 | 7 | 9 | 12 | 14 | 16 | 19 | 21 | 28 | 35 | 110 |
| M: Control | 5 | 2 | 2 | 2 | 1 | 1 | 1 | 1 | 1 | 1 | 1 | 1 | 1 | 1 | 1 | 0 |
| M: 30 μg/kg CM101 | 4 | 4 | 4 | 4 | 4 | 4 | 4 | 4 | 4 | 4 | 4 | 4 | 4 | 4 | 4 | 4 |
| M: 60 μg/kg CM101 | 6 | 6 | 6 | 6 | 6 | 6 | 6 | 6 | 6 | 6 | 6 | 6 | 6 | 6 | 6 | 4 |
| P: Control | 9 | 4 | 4 | 4 | 3 | 3* | 1 | 1 | 1 | 1 | 1 | 1 | 1 | 0 | 0 | 0 |
| P: 30 μg/kg CM101 | 8 | 8 | 8 | 8 | 7 | 7* | 5 | 5 | 5 | 5 | 5 | 5 | 5 | 5 | 5 | 5 |
| P: 60 μg/kg CM101 | 8 | 8 | 7 | 7 | 7 | 7* | 5 | 5 | 5 | 5 | 5 | 5 | 5 | 5 | 5 | 4 |

*Two mice from each group were sacrificed for histology on day 6

B. Recovery of Function at the Organismal Level

Figure 2A:
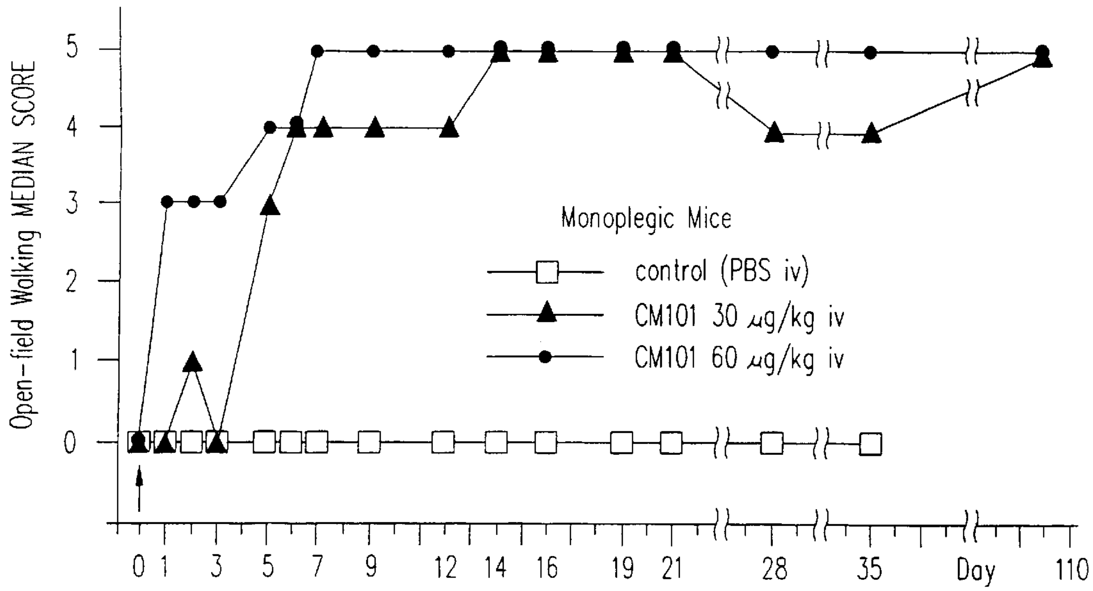
FIGS. 2A–2B depicts the recovery of hind limb function in monoplegic (A) or paraplegic (B mice from control (hollow square), 30 μg/kg CM101 (solid triangle), and 60 μg/kg CM101 (solid circle) groups. The median open-field walking scores of each group of mice are shown on the Y-axis, and the X-axis indicates the day on which the measurements were taken, wherein day 0 is the day of surgery. Scores were generated from the paralyzed limb in monoplegic animals (A). In paraplegic mice (B), individual animal scores were calculated by averaging scores from each hind limb.
Figure 2B:
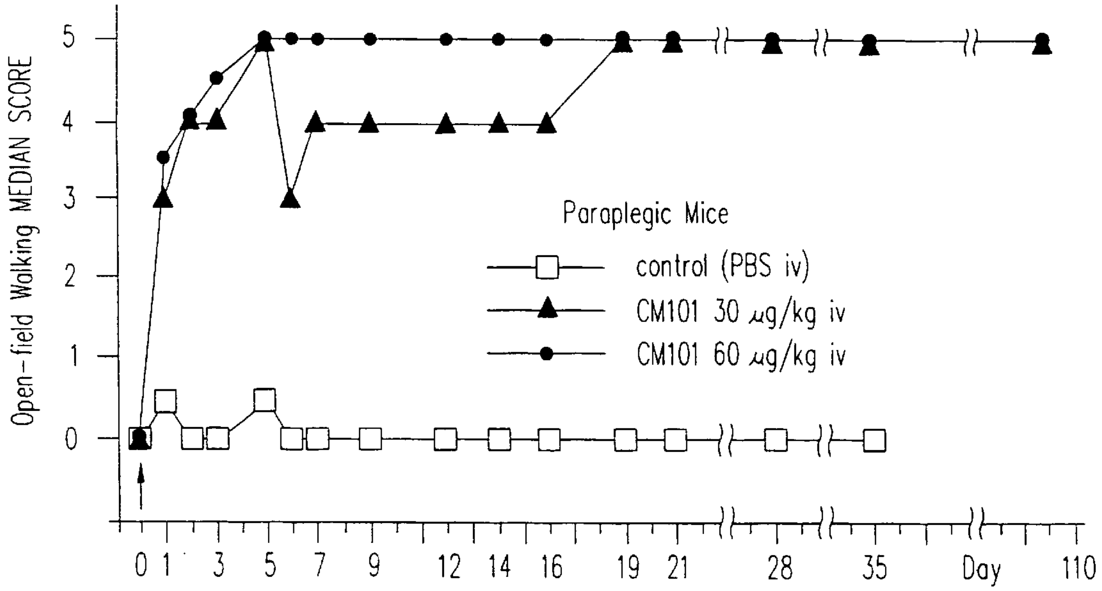

Recovery of walking ability in monoplegic and paraplegic animals is depicted in graphical form in FIGS. 2A and 2B, respectively. On the day of surgery, mice in all study groups were dragging their hind limb(s) (FIGS. 2A and 2B, arrowhead). By day 2, 7 of 10 treated monoplegic mice and 10 of 16 treated paraplegic mice displayed partial restoration of walking ability as evidenced by a open-field walking scores of at least 3. When the scores of monoplegic and paraplegic treated mice were compared to their respective control groups, the differences were significant (p<0.001 in Kruskal-Wallis test) in the paraplegic animals from day 3 forward (except for day 6) and in the monoplegic animals from day 6 forward. Full recovery of normal walking function was observed in 10 of 10 treated (30 μg/kg CM101, n=4; 60 μg/kg CM101, n=6) monoplegic mice by day 14, four days after the last CM101 treatment. Among the paraplegic mice, 7 of 8 mice receiving 30 μg/kg CM101 and 7 of 8 mice receiving 60 μg/kg CM101 showed improved walking ability meriting scores between 3 and 5 by day 12. Several treated animals were kept past 110 days; they retained scores of 5 (normal walking) and even regained control of their tails.

These data demonstrate that CM101 produces a remarkably rapid regeneration of the spinal cord in animals with acute spinal cord injury as evidenced by recovery of motor function within days of treatment.

C. Healing and Glial Scar Formation at the Cellular Level

MRI evaluation of the area of spinal damage on day 21 revealed marked differences in the healing process between control and treated animals. At the site of compression in each of the control animals, there was an obvious, large area of damage involving surrounding tissue and spinal cord. By comparison, the treated mice had very limited lesional areas. Thus, treatment with CM101 significantly reduced the region of compression-induced damage and scarring.

Spinal cord gliosis levels and overall recovery of tissue structure were determined by histopathological examination of tissue from treated and untreated animals. The results corroborated the MRI analysis: CM101-treated mice had significantly reduced areas of hemorrhage, gliosis and fibrosis compared to control mice.

Example 4

Treatment with CM101 Facilitates Neuronal Regeneration in Traumatized Spinal Cord Neurons in Culture The effect of CM101 on repair of neuronal injury was tested in cultured spinal cord and cortical neurons by assaying alteration in neuronal membrane potential following application of a pulse of gamma-amino-butyric-acid (GABA).

GABA, a major inhibitory neurotransmitter in the CNS, causes membrane potential hyperpolarization by opening chloride channels via $GABA_A$ receptors and reducing intracellular calcium levels via $GABA_B$ receptors. However, when neurons are injured by direct physical damage to the cell body or processes, they respond to a brief pulse of GABA by depolarizing their membrane potentials. The severity of the neuronal damage is reflected in the amplitude of the GABA-mediated depolarization. Since neuronal response to GABA is a metric of the degree of injury, GABA response can be used to assess the state of repair of injured neurons. In addition to documenting the normal recovery time-course of injured neurons, the assay was used to determine if CM101 affects regeneration of injured neurons.

Spinal cord cell cultures were prepared according to published methods (Wamil et al., Use-, concentration-, and voltage-dependent limitation by MK-801 of action potential firing frequency in mouse central neurons in cell culture, *J. Pharmacol. Exp. Ther.,* 260: 376–383 (1992)). Briefly, embryonic mouse spinal cords (gestational day 13–14) were minced and dispersed by trituration to single cells and small clumps. The neurons were plated on collagen-coated dishes and maintained in vitro at 35° C. for 4–16 weeks prior to experimentation. During the first week of culturing, the culture medium consisted of: 80% (v/v) Eagle's MEM supplemented with 5.5 mM glucose and 24 mM sodium bicarbonate; 10% fetal calf serum; and 10% heat-inactivated horse serum with 10 ng/ml 7S nerve growth factor and 1 ml/l Mito Serum Extender (all supplements from Collaborative Research, Bedford, Mass.). After equilibration with incubator atmosphere containing 10% $CO_2$, the pH of the culture medium was 7.4. The culture medium was changed three times a week. After one week, growth of non-neuronal cells was suppressed by brief treatment with 5-fluoro-2'-deoxyuridine. Thereafter, no horse serum was included in the culture medium.

The methods used here have been published in detail elsewhere (Wamil et al., Use-, concentration-, and voltage-dependent limitation by MK-801 of action potential firing frequency in mouse central neurons in cell culture, *J. Pharmacol. Exp. Ther.,* 260: 376–383 (1992); Wamil et al., Phenytoin Blocks N-Methyl-D-Aspartate Responses of Mouse Central Neurons, *J. Pharmacol. Exp. Ther.,* 267: 218 (1993)). Before experimentation, the culture medium was replaced with modified Dulbecco's phosphate-buffered saline (mDPBS) which contained elevated $Mg^{2+}$ concentrations to suppress spontaneous synaptic activity (composition in millimolar: NaCl, 143.4; KCl, 4.2; $CaCl_2$, 0.9; $MgCl_2$, 1.0–7.0; and glucose 5.6 in 9.5 mM sodium-phosphate buffer at pH 7.4). The culture dish was placed in a micro-incubation system (PDMI-2, Medical Systems Corp., Greenvale, N.Y.) with a temperature controlled at 37° C. by a bipolar temperature controller (TC-202, Medical Systems Corp., Greenvale, N.Y.) on the stage of an inverted phase contrast microscope (Nikon Diaphot 300). The cells were continuously perfused with mDPBS.

During the experiments, individual neurons were impaled with microelectrodes so that intracellular recordings of transmembrane potential could be made. A bridge circuit in the amplifier (Axoclamp 2B, Axon Instruments) allowed simultaneous injection of current and recording of potential.

Before the effect of GABA on membrane potential was investigated, the quality of the cultures was tested by applying (via the recording electrode) a series of depolarizing current pulses of 400 ms duration and variable amplitude to elicit overshooting action potentials (APs) in neurons with stable resting potentials ($E_m$) more negative than or equal to −55 mV. Sustained repetitive firing of action potentials and the $E_m$ measurement were criteria of neuron vitality. Neurons damaged during impalement had low resting potential, undershooting action potentials which did not increase in amplitude with hyperpolarizing current, and either limited firing during depolarizing steps or extremely fast spontaneous firing before loss of membrane potential and cell death. Such impalements were terminated and a new neuron was selected for study.

Neurons were injured via direct physical compression of processes or cell bodies by a heat-polished glass micropipette. Starting 5–10 minutes after the infliction of injury and continuing through this and subsequent electrophysiological experiments, one group of injured neurons was exposed to CM101 (0.1 to 6 μg/ml, CarboMed, Inc., Brentwood, Tenn.) in the superfusate. During the culturing periods that followed the experiments, these treated neurons received culture medium supplemented with 0.3 μg/ml CM101. The other group of injured neurons was not exposed to CM101.

Intracellular recordings of transmembrane potential were made 6 hours, 2 days, and 5 days after injury and at comparable times for uninjured control neurons. During the recording, 10 μM GABA (Research Biochemicals International, Natick, Mass.) was applied by 3s pressure application from a blunt micropipette made of a patch-clamp electrode. Drug application was rapidly terminated by continuous perfusion with drug-free buffer streaming in the opposite direction from that of the GABA application.

Results

Figure 3A:
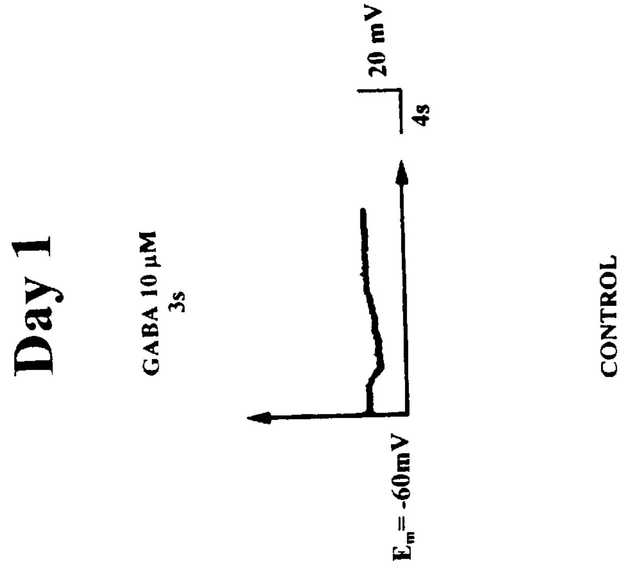
FIGS. 3A–3I show the effects of 3 second pulses of 10 μM GABA (horizontal lines below readout) on the membrane potential of control cultured mouse spinal cord neurons (A,D,G), traumatized neurons treated with 0.3 μg/ml CM101 (B, E,H), and untreated traumatized neurons (C,F,I). GABA pulses were applied 6 hours (A,B,C), two days (D,E,F), and five days (G,H,I) after injury. Calibrations at right apply throughout.

As expected, the application of 10 μM GABA to intact neurons after 12–16 weeks in culture produced a hyperpolarization of 8.6±0.7 SE mV for 10.0±1.2 s (FIGS. 3A, D, G; resting membrane potential, $E_m$=−67.5±2.7, n=10).

Untreated. neurons injured by direct physical damage to the cell body or processes are depolarized by a 3s pressure application of 10 μM GABA. Six hours after crush injury of a process, GABA reversibly depolarized the neuronal membranes of traumatized neurons 30 to 55 mV (FIG. 3C). Even 2 and 5 days after the damage was inflicted, fresh applications of 10 μM GABA caused depolarization (FIG. 3F & I, respectively). A minimum depolarization of 20 mV was recorded on day 5 of the experiment (FIG. 3I). Thus, in the days following an injury, traumatized neurons continue to depolarize in response to GABA application, but the amplitude and duration of the depolarization lessens with time.

Figure 3B:
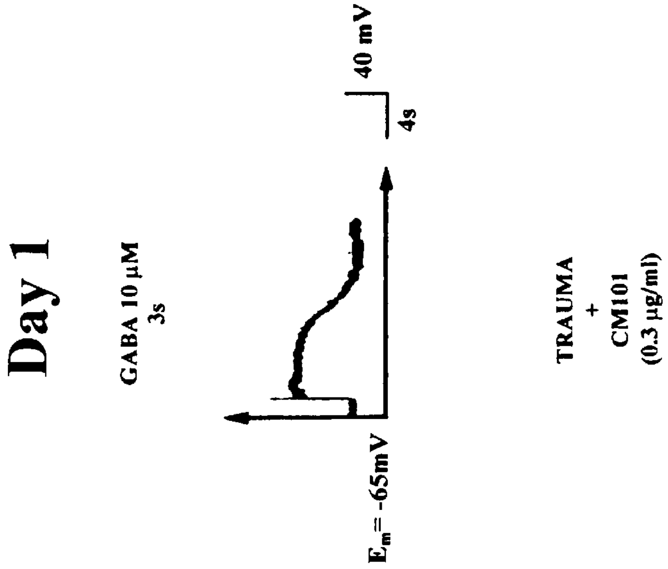
Figure 3C:
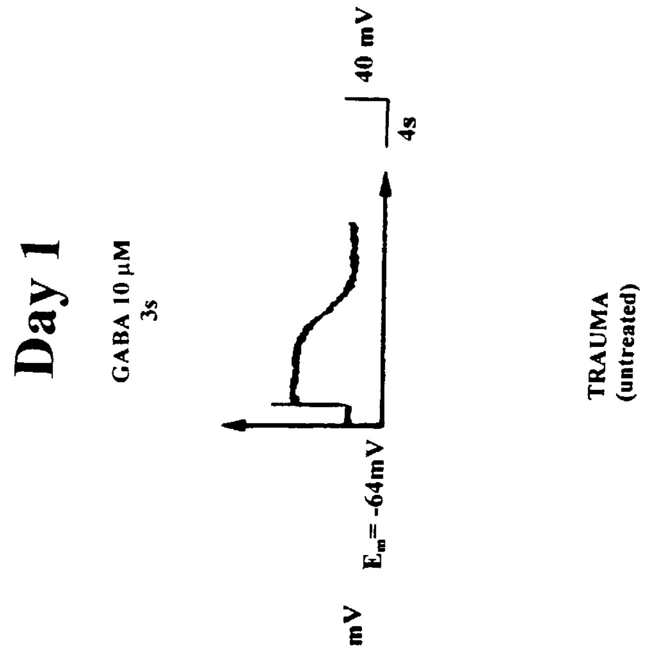
Figure 3F:
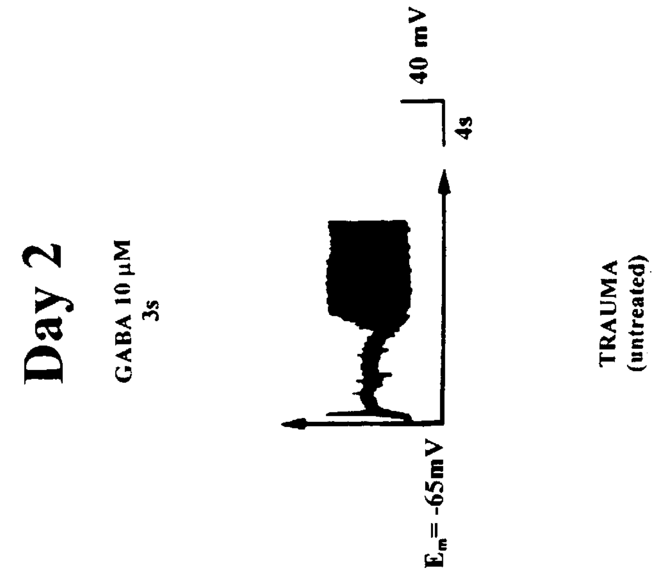
Figure 3E:
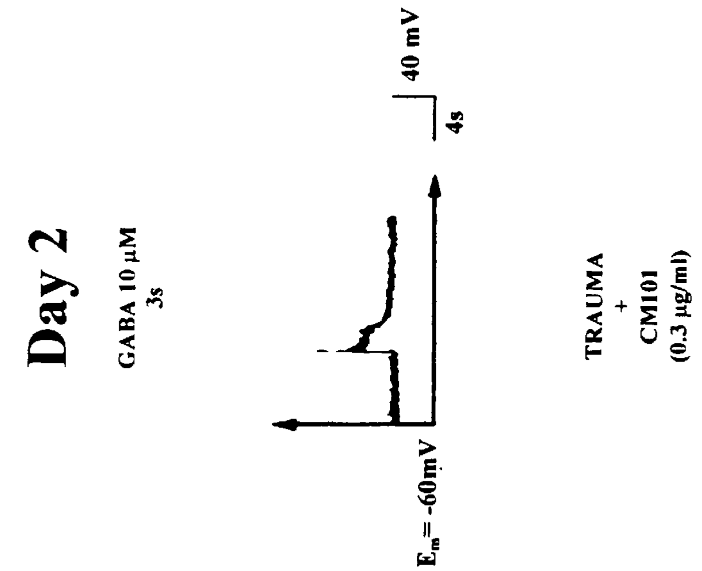
Figure 3D:
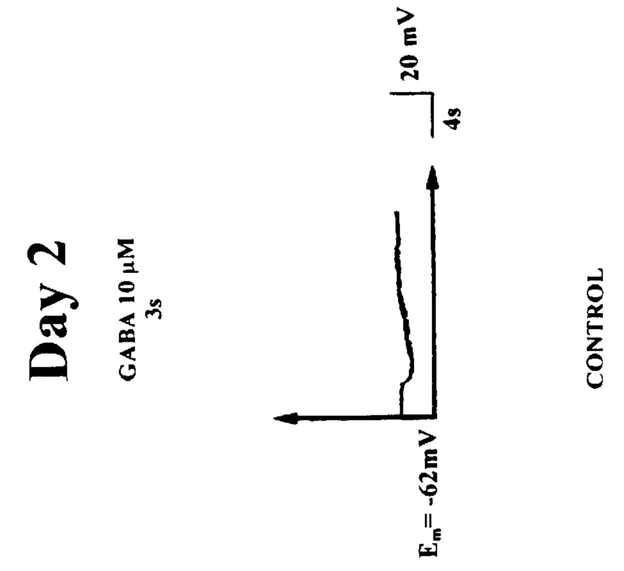
Figures 3G, 3H, 3I:
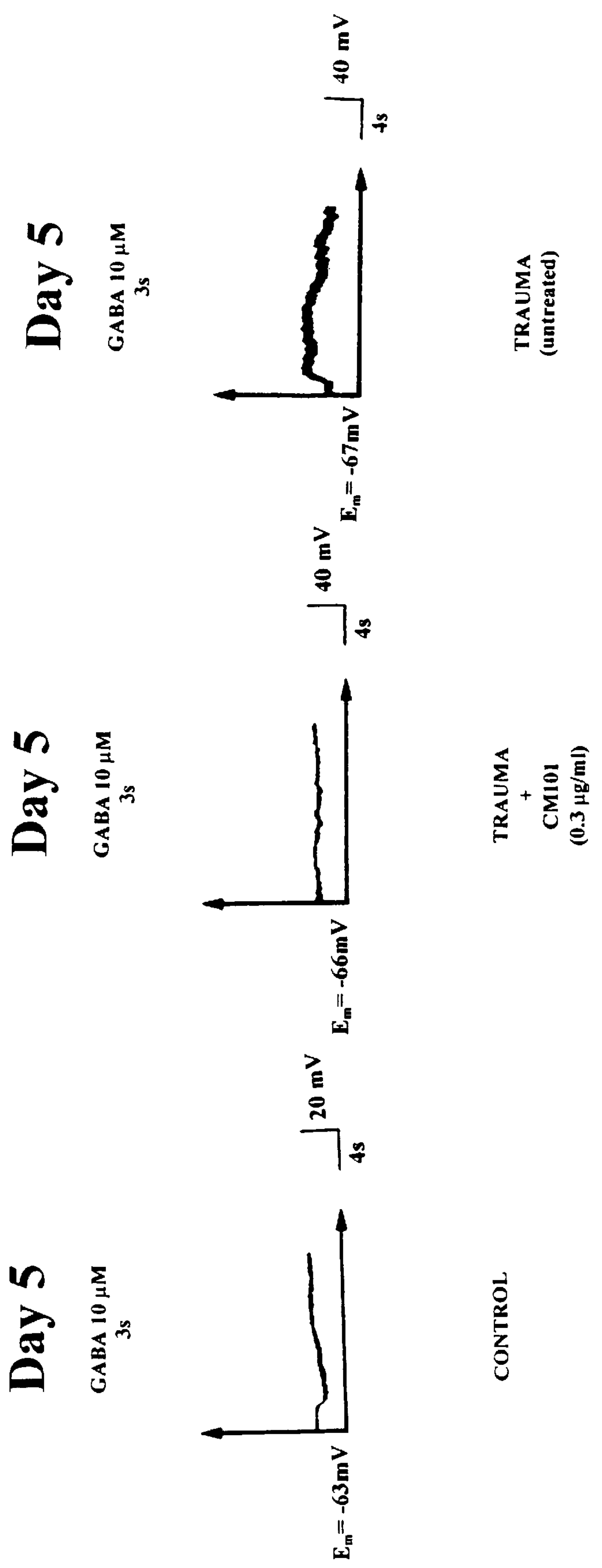

When GABA was applied 6 hours after injury, CM101-treated neurons responded by depolarizing (FIG. 3B). This depolarization was similar in amplitude and duration to that exhibited by untreated injured neurons upon exposure to GABA (compare FIGS. 3B and 3C). After neurons were treated with 0.3 μg/ml CM101 for two days following injury, GABA application caused membrane depolarization (FIG. 3E). However, the amplitude and duration of the depolarization were significantly diminished relative to the depolarization seen in untreated neurons two days after injury (compare FIG. 3E and 3F). After five days of continuous post-injury CM101 exposure, the traumatized neurons responded to GABA with a small depolarization (2 to 5 mV) and a small hyperpolarization (1 to 3 mV) (FIG. 3H). This response is more similar to the response of uninjured neurons to GABA than it is to the response to GABA of untreated neurons five days post-injury (compare FIG. 3H with FIGS. 3G and 3I).

These data show that the restoration of a physiologically normal hyperpolarizing response to GABA is facilitated by CM101. Thus, neuronal injuries are repaired more rapidly when CM101 is administered. This indicates that CM101 promotes neuronal regeneration.

These investigations provide in vivo, ex vivo, and in vitro evidence of enhanced neuronal regeneration and recovery of physiologic functions by injured neurons treated with CM101. CM101 treatment dramatically increases the probability that central nervous system injury victims will survive their injuries and regain neuronal function.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of treating a patient with a neutral injury, which method comprises:

administering to the patient a polysaccharide toxin from group B β-hemolytic Streprococces (GBS) bacteria in a quantity sufficient to at least partially inhibit scar formation by impairing glial cell proliferation.

2. A method of treating a patient with a preexisting neural injury having scar tissue, which method comprises:

excising the scar tissue, and administering a polysaccharide toxin from group B β-hemolytic Streptococcus (GBS) bacteria to the patient in a quantity sufficient to minimize scarring by impairing glial cell proliferation.

3. The method of claim 1 wherein the GBS polysaccharide toxin is substantially pure.

4. The method of claim 3 wherein the GBS polysaccharide toxin has a purity of at least approximately 90%.

5. The method of claim 1 wherein the neural injury is in the central nervous system.

6. The method of claim 5 wherein the neural injury is in the spinal cord.

7. The method of claim 5 wherein the neural injury is in the brain.

8. The method of claim 7 wherein the neural injury is in the cortex.

9. The method of claim 1 wherein the neural injury is in the peripheral nervous system.

10. The method of claim 1 wherein the neural injury is induced by trauma.

11. The method of claim 1 wherein the neural injury is induced by surgery.

12. The method of claim 1 wherein the neural injury is induced by ischemia.

13. The method of claim 1 wherein the GBS polysaccharide toxin is administered to the patient systemically.

14. The method of claim 13 wherein the GBS polysaccharide toxin is adminstered to the patient travenously.

15. The method of claim 13 wherein the GBS polysaccharide toxin is administered to the patient intra-arterially.

16. The method of claim 1 wherein the GBS polysaccharide toxin is administered to the patient intrathecally.

17. The method of claim 1 wherein the GBS polysaccharide toxin is administered to the patient within one day of infliction of an injury.

18. The method of claim 17 wherein the GBS polysaccharide toxin is administered to the patient within six hours of infliction of an injury.

19. The method if claim 2 wherein the patient is at least 7 days old.

20. The method of claim 1 wherein the GBS polysaccharide toxin is administered to the patient in a dosage of 1 μg/kg to 100 μg/kg body weight.

21. The method of claim 20 wherein the GBS polysaccharide toxin is administered to the patient in a dosage of between 1 μg/kg and 25 μg/kg body weight.

22. The method of claim 1 wherein GBS polysaccharide toxin is administered in a quantity sufficient to at least partially inhibit gliosis.

23. The method of claim 2 further comprising:

administering a compound to the patient to promote neural regeneration.

24. The method of claim 23 wherein the compound that promotes neural regeneration is selected from the group consisting of: IGF-1, bFGF, TGFβS, BDNF, NT-3 or CNTF.

25. The method of claim 2 further comprising:

transplanting neural progenitor cells in proximity to the site of excision.

26. The method of claim 2 wherein the GBS polysaccharide toxin is substantially pure.

27. The method of claim 26 wherein the GBS polysaccharide toxin has a purity of at least approximately 90%.

28. The method of claim 2 wherein GBS polysaccharide toxin is administered in a quantity sufficient to at least partially inhibit gliosis.

29. The method of claim 2 wherein the neural injury is in the spinal cord.

30. The method of claim 2 wherein the neural injury is in the brain.

31. The method of claim 1, wherein the GBS polysaccharide toxin provides biological activity as evidenced by induction of respiratory distress in a sheep assay or activation of complement and binding to neovasculature in a peroxidase-antiperoxidase assay of a tumor tissue specimen.

32. The method of claim 2, wherein the GBS polysaccharide toxin provides biological activity as evidenced by induction of respiratory distress in a sheep assay or activation of complement and binding to neovasculature in a peroxidase-antiperoxidase assay of a tumor tissue specimen.

* * * * *